United States Patent
Taub

(10) Patent No.: US 11,344,638 B2
(45) Date of Patent: May 31, 2022

(54) COMPOSITION FOR RADIATION TREATMENT OF INTRACAVITARY OR METASTATIC DEPOSITS OF MALIGNANCY AND METHOD FOR TREATMENT THEREWITH

(71) Applicant: Robert Norman Taub, New York, NY (US)

(72) Inventor: Robert Norman Taub, New York, NY (US)

( * ) Notice: Subject to any disclaimer, the term of this patent is extended or adjusted under 35 U.S.C. 154(b) by 0 days.

(21) Appl. No.: 17/208,970

(22) Filed: Mar. 22, 2021

(65) Prior Publication Data

US 2021/0290786 A1 Sep. 23, 2021

Related U.S. Application Data

(60) Provisional application No. 62/992,425, filed on Mar. 20, 2020.

(51) Int. Cl.
*A61K 51/06* (2006.01)
*A61K 51/12* (2006.01)
*A61K 51/04* (2006.01)

(52) U.S. Cl.
CPC ........ *A61K 51/065* (2013.01); *A61K 51/0482* (2013.01); *A61K 51/1213* (2013.01)

(58) Field of Classification Search
CPC ............. A61K 51/065; A61K 51/0482; A61K 51/1213
See application file for complete search history.

(56) References Cited

U.S. PATENT DOCUMENTS

| 5,422,095 | A | 6/1995 | Hashiguchi et al. |
| 5,514,379 | A | 5/1996 | Weissleder et al. |
| 6,670,456 | B2 | 12/2003 | Frank et al. |
| 2003/0003048 | A1* | 1/2003 | Li ...................... A61K 47/6889 424/1.49 |
| 2016/0331853 | A1 | 11/2016 | Taub |
| 2019/0216956 | A1 | 7/2019 | Taub et al. |

FOREIGN PATENT DOCUMENTS

| EP | 0326226 A1 | 8/1989 |
| WO | 8702893 A1 | 5/1987 |
| WO | 2017120193 A1 | 7/2017 |
| WO | 2018022929 A1 | 2/2018 |

OTHER PUBLICATIONS

Guo et al., ACS Appl Mater Interfaces 2017, 9, 23508-23519. (Year: 2017).*
Mehvar, Dextrans for targeted and sustained delivery of therapeutic and imaging agents, Journal of Controlled Release 69, 1-25, 2000.
Orcutt, Protein Engineering for Targeted Delivery of Radionuclides to Tumors, submitted to the Department of Chemical Engineering in particular fulfillment of the requirements for the degree of Doctor of Philosophy in Chemical Engineering at the Massachusetts Institute of Technology, Dec. 2009.
Pawar et al., Polysaccharides as carriers of bioactive agents for medical applications, Natural-based polymers for biomedical applications, 3-53, 2008.
Holmberg et al., Ion Exchange Tumor Targeting: A New Approach, Clinical Cancer Research, vol. 5, 3056s-3058s, Oct. 1999.
USPTO Office Action dated Oct. 27, 2020, for Robert Norman Taub, U.S. Appl. No. 16/815,759, filed Mar. 11, 2020.
USPTO Final Office Action dated May 14, 2021, for Robert Norman Taub, U.S. Appl. No. 16/815,759, filed Mar. 11, 2020.
International Search Report dated Jul. 28, 2021, for Robert Taub, International Application No. PCT/US21/23520, filed Mar. 22, 2021.
Written Opinion of the International Search Authority dated Jul. 28, 2021, for Robert Taub, International Application No. PCT/US21/23520, filed Mar. 22, 2021.

* cited by examiner

*Primary Examiner* — Robert S Cabral
(74) *Attorney, Agent, or Firm* — Law Offices of Albert Wai-Kit Chan, PLLC; Robert D. Katz, Esq.

(57) ABSTRACT

The invention provides a compound having the following structure:

T-DOTA-R, wherein T is a carbohydrate polymer, R is a radioactive isotope, DOTA is a chelator of R, and T is covalently bond to DOTA. In one embodiment, the carbohydrate polymer is hyaluronic acid (HA). The compound or HA is used alone as a polymer or incorporated into a hydrogel for treating body cavity cancer, comprising administering an effective amount of the compound or hydrogel. The invention also provides a method for treating body cavity or soft tissue cancer comprising: introducing into the affected area a thermo reversible gel comprising the compound or HA, allowing the radioactive isotope to emit a therapeutic radiation to affected regions; and, after a predetermined time, optionally removing the gel from the body cavity with a cold rinse to liquefy the gel and allow it to exit the body cavity.

11 Claims, 2 Drawing Sheets

DOTA

COMPOSITION FOR RADIATION TREATMENT OF INTRACAVITARY OR METASTATIC DEPOSITS OF MALIGNANCY AND METHOD FOR TREATMENT THEREWITH

CROSS-REFERENCE TO RELATED APPLICATION

This application claims the benefits of U.S. Ser. No. 62/992,425, filed Mar. 20, 2020. The entire contents and disclosures of the prior application are incorporated herein by reference into this application.

Throughout this application, various references are referred to and disclosures of these publications in their entireties are hereby incorporated by reference into this application to more fully describe the state of the art to which this invention pertains.

FIELD OF THE INVENTION

This invention relates to a composition comprising radioisotope chelates and methods for treating malignancies in body cavities and other locations using such radioisotopes.

BACKGROUND OF THE INVENTION

Irradiation of localized cancer has long been known as an effective means of treatment that must be engineered to avoid damaging adjacent healthy tissue. This is especially true for tumors involving body cavities such as the urinary bladder, the peritoneum, pleural cavity, pericardium, and synovial joint capsule. Such tissues are adjacent to vital highly radiosensitive organs such as the heart, the kidneys and the intestines. It is difficult to avoid damage to healthy tissues from externally applied radiation that travels in a straight line to an irregular cavitary target. While it has been known for some time that intravascularly injected radioactive macromolecules could be useful for diagnostic imaging and tumor targeting, this invention moves away from the diagnostic to the therapeutic realm and proposes treatment of inner cavitary surfaces or even metastatic nodules confined to a poorly accessible soft tissue space using a membrane-impermeable conformable gel as a carrier for a radioisotope source. This approach presents advantages over available treatment techniques. Previous attempts at such treatment employed intravenously injected small molecule radioisotope carriers that passed through the entire body, a fraction of which eventually attached to an intended target by linking up with specific antibodies. Other approaches involved localized administration of chemotherapy agents coupled to a biocompatible matrix to form a treatment solution, but were limited by the barrier to diffusion of the drug posed by the poorly permeable bladder mucosa. For example, U.S. Pat. No. 9,884,028 (Holzer); U.S. Pat. No. 10,471,150 (Konorty); and European Patent Specification No. EP 525 777 B1 (Holzer) discuss such an approach for coating an internal cavity with a treatment solution. The treatment solution can include a solidifiable matrix that is coated on the interior of an internal cavity, and acts a slow-release delivery system for such common chemotherapy agents as Taxol, doxorubicin, or mitomycin C. The foregoing patents and applications, as well as any of the cited references below, are incorporated by reference herein with the same force and effect as set forth herein. The present invention seeks to remedy the deficiencies of previous methods used to treat cancer and other diseases in internal cavities, while protecting unaffected areas.

There are several obstacles and complications known that accompany the presently used methods for topical treatments for bladder cancer: (1) the Mucosal Membrane: One of the physiological purposes of the mucosal membrane that covers the bladder's inner wall, which is permanently soaked in urine (i.e., a watery distended bladder; and the rate of release of the therapeutic agent is determined by the concentration of the agent and the rate of degradation of the material.

Radiation treatment of the peritoneal cavity afflicted by variably thick coatings of primary peritoneal or metastatic implants that have spread over its inner surface might also be improved by using a radioactive solution of radioisotope which would remain localized and conforming to the internal surface area of treatment without excessive systemic leakage.

There is accordingly a need for a composition and treatment method that can deliver radiotherapy localzly to a controlled depth of tissue in an affected body cavity such as the urinary bladder or peritoneal cavity yet limits penetration of the radioactivity through the membranes of the body cavity and into adjacent organs, tissues, or the bloodstream of the patient.

SUMMARY OF THE INVENTION

In one embodiment the invention provides a compound having the following structure:

T-DOTA-R, wherein T is a high molecular weight (100,000 to greater than 3 million) polymer and is covalently bound to dodecane tetra-acetic acid (DOTA) or a similar radioisotope chelator such as Pentetic Acid (DTPA), and R is a radioactive isotope. In our estimation, commonly used carbohydrates suitable for this purpose include carboxymethylcellulose (CMC) and hyaluronic acid (HA). Either compound may be used as a single DOTA-conjugated radioactive polymer, or as a hydrogel in combination with other carbohydrates to optimize properties of viscosity, adhesion, reverse thermal gelation, and tissue stability. The high molecular weight of such agents renders them near- or totally unable to penetrate through body cavity membranes. In the following listed embodiments specifically mentioning hyaluronic acid, amine-derivatized CMC can also be considered for use as the radioactive polymer. In one embodiment, the percentage of HA in the HA-DOTA-R alone composition is about 0.1-1.0% (w/w). In one embodiment, the composition comprises HA as carrier with a percentage of 0.1-1.0% (w/w).

In one embodiment HA-DOTA-R is used as a single agent, in concentrations of 0.1-1.0%. In other embodiments, the invention involves formation of radioactive HA-DOTA-R crosslinked in solution at temperatures 20-37 degrees Celsius with hydrogel comprising between 20% and 30% (w/w) ethylene oxide/propylene oxide block copolymer; between 0.1% and 0.3% (w/w) reverse-thermal Hipromellose (HPMC), between 0.1% and 1.8% (w/w); and/or PEG-400, 0.1-0.5%, with the balance water. In another embodiment, the thermo-reversible polymer hydrogel component comprises 0.05% to 0.8% carboxymethylcellulose (CMC), 0.1% to 2.5% PEG 400, and 18% to 40% (w/w) ethylene oxide/propylene oxide block copolymer, with the balance water. In a further embodiment, the thermo-reversible polymer hydrogel comprises HA-DOTA-R 0.1-1.0%, 12-30% Pluronic F127; 5-30% Pluronic F68; 0.05% and 2% (w/w) CMC; and between 0.1% and 2.5% (w/w) PEG-400; with the balance water. In yet another embodiment, the radioactive isotope is Yttrium-90, Technetium-99 (m), Gadolinium-66, actinium-225, lutetium-177, indium-111, bismuth 213, among others. In one embodiment, the composition is in a form of hydrogel liquid at 37 degrees. In yet another embodiment, the hydrogel comprises one or more thermo-reversible polymers. In yet another embodiment, the thermo-reversible polymers comprise a cellulose or derived cellulose, and wherein the cellulose or derived cellulose is hydroxypropyl methylcellulose (HPMC), hydroxypropyl cellulose (HPC), low-substituted hydroxypropyl cellulose, or hydroxypropyl methylcellulose acetate succinate (HPMCAS). The invention also provides an embodiment wherein the thermo-reversible polymer hydrogel comprises ethylcelluloses, cellulose acetate or cellulose acetate butyrate or any combination thereof or hydroxyethyl celluloses (HEC), methyl cellulose (MC), carboxymethyl cellulose (CMC), and their salts. In one embodiment, the gelation temperature of the hydrogel ranges from 20° C. to 37 degrees C.

In another embodiment, the invention also provides a composition of matter comprising an effective cancer therapeutic amount of a thermo-reversible polymer functionalized with ethylene triamine, then covalently bound to dodecane tetra-acetic acid (DT or DOTA) or a conjugate base thereof and is bound to R, wherein R is a radioactive isotope. In one embodiment, the invention provides a composition of matter in a form of thermo-reversible polymer hydrogel comprising between 20% and 30% (w/w) ethylene oxide/ propylene oxide block copolymer, between 0.1% and 0.3% (w/w) HPMC, between 0.1% and 1.8% (w/w) PEG-400, with the balance water. In a further embodiment, the method treats cancer in a body cavity such as bladder cancer, peritoneal cancer, appendiceal carcinoma, or ovarian carcinoma. In a further embodiment, the method comprises treating body cavity cancer in a patient afflicted therewith by administering an effective amount of a thermo-reversible hydrogel incorporating Hyaluronic acid—DOTA-radioactive isotope compound. Preferably, the thermo-reversible polymer comprises a hydroxypropyl cellulose polymer or derivative and the radioactive isotope is Yttrium-90, Technetium-99(m), Gadolinium-86, actinium-225, lutetium-177, indium-111, or Bismuth 213. In another embodiment, the thermo-reversible polymer hydrogel comprises hydroxypropyl methylcellulose and the radioactive isotope is Yttrium-90 or Technetium-199(m). In yet another embodiment, the invention comprises administering an effective amount of the hydrogel complex such that the body cavity cancer receives between about 30 Gy of radiation to affected tissue.

In yet a different embodiment, the invention provides a method for treating body cavity cancer comprising introducing into the body cavity of a hydrogel in which radioactive Hyaluronic acid-DOTA-isotope gel comprising an effective amount of isotope is complexed with a thermorreversible carbohydrate to form a hydrogel which would allow radiation emitted by the radioactive isotope to penetrate cancer cells located in the body cavity for a predetermined time, followed by removing substantially all of the gel from the body cavity with a cold rinse to liquefy the reverse thermosensitive gel and allow it to exit the body cavity.

BRIEF DESCRIPTION OF THE DRAWINGS

Other features and advantages of the invention will become apparent upon review of the following detailed description of the preferred embodiments taken in conjunction with the attached drawings, in which.

DETAILED DESCRIPTION OF THE PREFERRED EMBODIMENTS

Figure 1:
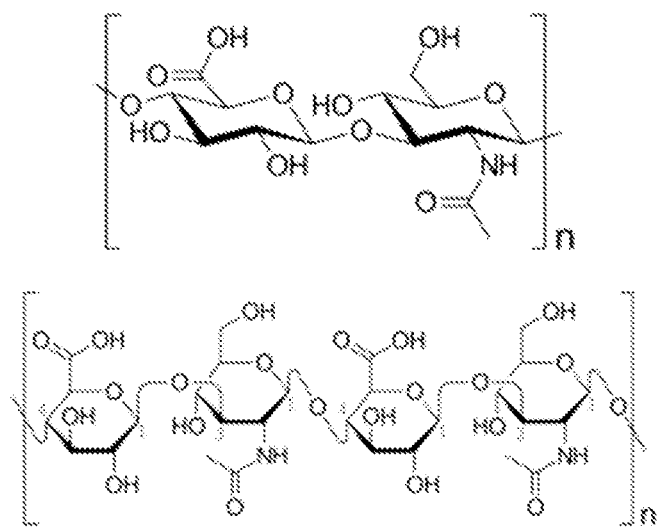
FIG. 1 is a structural diagram of a hyaluronic acid molecule.
Figure 2:
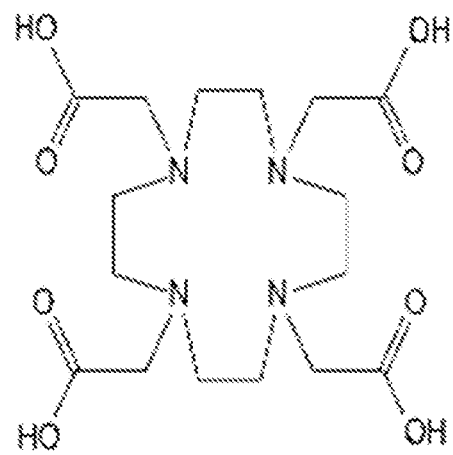
FIG. 2 is a structural diagram of a dodecane tetraacetic acid molecule.
Figure 3:
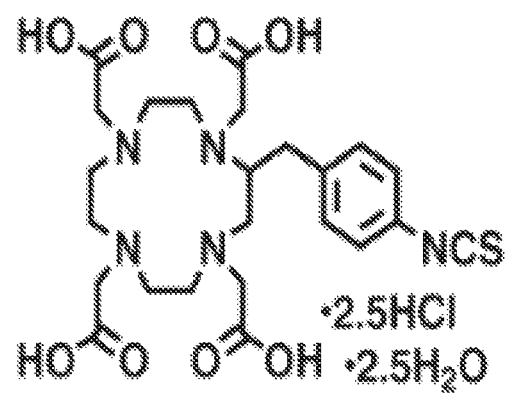
FIG. 3 is a structural diagram of an S-2,(4-isothiocyanatobenzyl)-1,4,7,10-tetraazacyclododecane tetraacetic acid molecule.

Hyaluronic acid, also called hyaluronan, is an anionic, nonsulfated glycosaminoglycan distributed widely throughout the extra-cellular matrix of connective, epithelial, and neural tissues. It can be very large: human synovial HA averages about 7 million Da per molecule, or about 20,000 disaccharide monomers. The average 70 kg (154 lb) person has roughly 15 grams of hyaluronan in the body, one-third of which is turned over (i.e., degraded and synthesized) per day. Hyaluronic acid is a major component of articular cartilage and synovial fluid; HA is known to increase the viscosity of the fluid. (Fraser J R, Laurent T C, Laurent U B (1997). "Hyaluronan: its nature, distribution, functions and turnover". J. Intern. Med. 242 (1): 27-33. PMID 9260563; Stern R (2004). "Hyaluronan catabolism: a new metabolic pathway". Eur. J. Cell Biol. 83 (7): 317-25. PMID 15503855)

While it is abundant in extracellular matrices, hyaluronan also contributes to tissue hydrodynamics, movement and proliferation of cells, and participates in a number of cell surface receptor interactions, notably those including its primary receptors, CD44 and RHAMM. hyaluronan degradation products may transduce an inflammatory signal through toll-like receptor 2 (TLR2, and thereby may play a role in innate immunity. Hyaluronic acid is a main component of the extracellular matrix, and has a key role in tissue regeneration, inflammation response, and angiogenesis, which are phases of skin wound repair (Shaharudin, A.; Aziz, Z. (2 Oct. 2016). "Effectiveness of hyaluronic acid and its derivatives on chronic wounds: a systematic review". Journal of Wound Care. 25 (10): 585-592. PMID 27681589.)

In gel form, hyaluronic acid combines with water and swells, making it useful in skin treatments as a dermal filler for treating facial wrinkles lasting about 6 to 12 months, a clinical treatment with regulatory approval by the US Food and Drug Administration ("Dermal Fillers Approved by the Center for Devices and Radiological Health". U S Food and Drug Administration. 26 Nov. 2018.)

A Joint Hydration Supplement That Uses Hyaluronic Acid

Granulation tissue is the perfused, fibrous connective tissue that replaces a fibrin clot in healing wounds. It typically grows from the base of a wound and is able to fill wounds of almost any size it heals. HA is abundant in granulation tissue matrix. A variety of cell functions that are essential for tissue repair may attribute to this HA-rich network. These functions include facilitation of cell migration into the provisional wound matrix, cell proliferation, and organization of the granulation tissue matrix. Initiation of inflammation is crucial for the formation of granulation tissue; therefore, the pro-inflammatory role of HA as discussed above also contributes to this stage of wound healing (Litwiniuk, M; Krejner, A; Speyrer, M S; Gauto, A R;

Grzela, T (2016). "Hyaluronic acid in inflammation and tissue regeneration". Wounds. 28 (3): 78-88. PMID 26978861.)

Apart from its physiologic ubiquity, and its function in tissue lubrication and cell physiology, HA is not used for treatment of any disease, and is regarded principally as a tissue scaffolding carbohydrate. playing important supporting roles in epidermal skin and synovial fluid.

Hyaluronic acid is a polymer of disaccharides, which are composed of D-glucuronic acid and N-acetyl-D-glucosamine, linked via alternating β-(1→4) and β-(1→3) glycosidic bonds. Hyaluronic acid can be 25,000 disaccharide repeats in length. Polymers of hyaluronic acid can range in size from 5,000 to 20,000,000 Da in vivo. The average molecular weight in human synovial fluid is 3-4 million Da., and hyaluronic acid purified from human umbilical cord is 3,140,000 Da; other sources mention average molecular weight of 7 million Da for synovial fluid. Hyaluronic acid also contains silicon, ranging between 350 µg/g to 1,900 µg/g depending on location in the organism (Schwarz, K. (1973 May 1). "A bound form of silicon in glycosaminoglycans and polyuronides". Proceedings of the National Academy of Sciences of the United States of America. 70 (5): 1608-1612. Bibcode:1973PNAS . . . 70.16085. PMID 4268099.)

Methods of Use

In the method proposed, a high molecular weight temperature-sensitive gel, safe, biologically inert and membrane-impermeable, is itself weaponized by the addition of covalently bound chemical chelators of radioactive isotopes exemplified by DOTA (see figure). This thermally-controlled conformable radiation source can be introduced into a warm cavity and optionally withdrawn from a diseased cavity such as a cancerous urinary bladder or abdomen using cold irrigation. Such a gel conceivably could be injected as a liquid into a soft tissue metastatic nodule in which it instantaneously gels and is immobilized. Because of its large molecular size and inability to cross cavity membranes, the dosage of administered radioactivity will be limited and defined by the contours, regular or irregular, of the body cavity or tissue into which it is injected, and the time during which it is permitted to remain. Normal organs will be largely spared. The rheological properties (viscosity, thixotropy, G', G") required for the introduction of the material into the internal cavity include: Adhesion—required to coat dependably the target tissue; Flexibility—to comply with the volume and shape natural changes of the internal cavity under treatment; Mechanical properties—such as hardness, tensile strength; and duration of time that the material remains in the internal cavity before it degrades.

In order to be regarded as a true medical device, however, rather than a drug or biologic, the proposed gel contains no attached or solubilized solution, or electrostatically immobilized active pharmaceutical ingredient (API), and its sole mode of action is by therapeutic irradiation of a covalently-bound chelated radioisotope. This feature distinguishes this conjugate from all other proposed gel conjugates proposed for intracavitary cancer treatment.

After treatment of the bladder, for example, and after the material degrades, it is excreted from the application site. Other sites such as nasal sinus, paranasal sinus, gallbladder, pleural cavity, vagina, uterus, renal pelvis, abdominal cavity, peritoneum, pelvic cavity, spinal thecal cavity, or synovial cavities might require incisional or trocar cold washout or drainage at a selected time point of treatment.

DOTA (for dodecane tetraacetic acid, short for 1,4,7,10-Tetraazacyclododecane-1,4,7,10-tetraacetic acid, a.k.a. tetraxetan) is shorthand for both the tetracarboxylic acid and its various conjugate bases. The four secondary amine groups are modified by replacement of the N-H centers with $N-CH_2CO_2H$ groups. The resulting aminopolycarboxylic acid, upon ionization of the carboxylic acid groups, is a high affinity chelating agent for di- and trivalent cations. As a polydentate ligand, DOTA envelops metal cations, especially the lanthanides such as Yttrium and in such complexes DOTA functions as an octadentate ligand, binding the metal through four amine and four carboxylate groups. Most such complexes feature an additional water ligand, giving an overall coordination number of nine. DOTA can be conjugated to the glucose residues of the cellulose in the hydrogel by attachment of one of the four carboxyl groups as an amide, although other configurations are possible. The remaining three carboxylate anions are available for binding to the Yttrium ion. The conjugate base of a functionally related chelating agent, Pentetic Acid (DTPA) also has a high affinity for metal cations. The penta-anion $DTPA^{5-}$ is potentially an octadentate ligand assuming that each nitrogen centre and each $COO^-$-group counts as a centre for coordination. As a chelating agent, DTPA wraps around a metal ion by forming up to eight bonds. Its complexes can also have an extra water molecule that coordinates the metal ion. (Deblonde, Gauthier J.-P.; Kelley, Morgan P.; et. al. (2018). "Spectroscopic and Computational Characterization of Diethylenetriaminepentaacetic Acid/Transplutonium Chelates: Evidencing Heterogeneity in the Heavy Actinide (III) Series". Angewandte Chemie International Edition. 57 (17): 4521-4526. PMID 29473263.) Transition metals, however, usually form less than eight coordination bonds. So, after forming a complex with a metal, DTPA still has the ability to bind to other reagents, as is shown by its derivative pendetide. (V. V. Fomenko, T. N. Polynova, M. A. Porai-Koshits, G. L. Varlamova and N. I. Pechurova *Crystal structure of copper (II) diethylenetriaminepentaacetate monohydrate* Journal of Structural Chemistry, 1973, Vol. 14, 529.)

CONJUGATION—Formation of DOTA-Gel-Y (CoGelrad-Y®): Earlier techniques of conjugation involved procedures for binding of carboxymethylcellulose to DOTA has undergone much change over the past two decades. More recently the synthesis has been facilitated by the availability of a DOTA precursor, p-SCN-Bn-DOTA (Chemical Formula. $C_{24}H_{33}N_5O_8S.2.5HCl.2.5H_2O$; Chemical Name: S-2-(4-isothiocyanatobenzyl)-1,4,7,10-tetraazacyclododecane tetraacetic acid.) This bifunctional reagent can directly couple to the cellulose moieties, such as those found in the structure of carboxymethylcellulose and hydroxypropyl methylcellulose. The reaction can take place over several hours at 30-50 degrees C., and the resulting product is purified by dialysis.

The DOTA moiety has proven effective and practical for achieving tight integration between Yttrium-90 and a wide variety of protein substrates, and the same conditions for chelation may be employed for ethylene-triamine-amino-derivatized-hipromellose, or carboxymethylcellulose substrates. Ammonium acetate buffer (0.5 M) is associated with a high uptake of Yttrium. The time required to chelate 94% of (four half-times) under prospective radiopharmacy labeling conditions in 0.5 M ammonium acetate may be up to three hours at pH 6.5, but less than 15 min at pH 7.5. Also, raising the reaction temperature from 25° C. to 37° C. may increase the chelation rate. Suggested radiolabeling conditions for initial evaluations of percent labeling efficacy are:

30-min reaction time, 0.5 M ammonium acetate buffer, pH 7-7.5 and 37° C. After the optional addition of DTPA (diethylenetriaminepentaacetic acid, a chelator) to remove any unbound Yttrium-90, the product is purified by column chromatography.

The person skilled in the art can appreciate that the invention provides several closely related methods to improve upon current radiotherapy of body cavities by providing the novel alternative of a reverse-thermal gel-bound radioisotope injected and confined within a cavity in which it can irradiate surfaces that have been involved by tumor, after which the isotope carrier can be liquefied and washed free of the target simply by lowering the temperature.

Specifically, the invention employs a DOTA- or DTPA-functionalized known tissue component, hyaluronic acid, either used as a polymer or in another embodiment as a radioactive carrier component of a crosslinked carbohydrate reverse-thermal hydrogel to localize Yttrium-90 or other radioactive isotopes in close proximity to inner surfaces of body cavities so as to impart a relatively uniform, assayable and optionally removable source of radiation. In one embodiment, hyaluronic acid is from human umbilical cord with an average molecular weight of 100,000 (Sigma Chemical Co.)

The bifunctional approach to labelling with radioactive metal isotopes uses bifunctional reagents for conjugation of the hyaluronic acid molecule and chelation of the radionuclide, selected by the nature of the radiometal, stability of the complex in high yield, and resistant to degradation/dissociation in the intended environment over the period of exposure. Hopefully, attachment of the reagent should be easily accomplished without much disturbance of the biological properties of the molecule. In one approach (D. Kozikova et al. Preparation and the kinetic stability of hyaluronan radiolabeled with 111In, 125I and 14C, Journal of Pharmaceutical and Biomedical Analysis 52 (2010) 517-524), an aqueous solution of DTPA is activated by 1-ethyl-3-(3-dimethylaminopropyl)carbodiimide (EDC) at pH 5-6. Dihydrazide of adipic acid (ADH) was used as a linker in the reaction. The reaction mixture was stirred for 6 h at room temperature. Secondly, HA was activated by cyanogen bromide at basic pH 9-10 and a low temperature (−10 to −5° C.). 6 min after activation of HA, a hydrazido-derivative of DTPA was added and stirred for 20 h at room temperature. The amine group of the linker reacted with one of the hydroxyl groups in HA via the carbonyl group to form adduct DTPA-HA. The product is purified by dialysis and lyophilized DTPA-HA is dissolved in 20 mL of de-mineralized water and dialyzed (cut-off 3500 g/mol) against 0.1% (w/v) NaOH and 0.1% (w/v) NaHCO3 for three days, and then against de-mineralized water for four days. The synthesized DTPA-HA is of MW 80-100 kDa and Degree of Substitution is about 4.5%. Such a preparation, stable for 48 hrs at urinary pH, could be used for Yttrium90 irradiation of the urinary bladder, and could be removed by evacuation possibly assisted by a solution of hyaluronidase. An alternate synthesis is contemplated using S-2-(4-Isothiocyanato-benzyl)-1,4,7,10-tetraazacyclododecane tetraacetic acid (P-Scn-BN-DOTA, Macrocyclics, Plano Tex.) which might yield a more stable chelate with Yttrium-90, following a similar procedure as illustrated above, wherein one end of a linker such as ADH is allowed to couple with p-SCN-BN-DOTA through a thiourea moiety. See, for examples, S. Hermanto et al., J. Radiation Research and Applied Sciences (DOI: 10.1016/j.jrras.2016.07.001); and J. Klein et al., Organic Letters, 2012, 14 (1), 330-333.

In one embodiment, 0.1 to 1% HA-DOTA-Yttrium used as a single agent at room temperature is injected into the bladder in patients afflicted with advanced refractory superficial non-muscle invasive bladder cancer, and flushed out of the bladder after a predetermined period, usually four hours In a second embodiment, the invention, used as a single agent in concentrations of up to 1% provides radiotherapy to superficial layers of peritoneum afflicted by widespread miliary, layered, or surface tumors originating in the distal fallopian tube of the ovary and in which patients have undergone prior surgical debridement and omentectomy. In a third embodiment, in cases of peritoneal involvement by various other tumors known to be relatively confined to the peritoneal cavity for long periods before dissemination through the body, such as inter alia, appendiceal carcinoma, primary peritoneal carcinoma, and peritoneal mesothelioma, among others, and in whom tumor debulking and peritonectomy have been performed. In a fourth embodiment, the single agent polymeric conjugate serves as an alternative means of irradiating the synovial cavity of patients suffering from advanced proliferative or neoplastic synovial secretory inflammation. In a fifth embodiment, the HA 0.1-1.0% is incorporated into a reverse thermal gel consisting of Hydroxypropylmethylcellulose 0.5-4%, carboxymethylcellulose 0.01-0.5% or dextran 0.0-05%, injected at a temperature of 20 degrees as a liquid, directed to difficult-to-resect-or-irradiate abdominal recesses, such as the area surrounding the superior mesenteric artery after Whipple resection; in those instances, the gel is exposed to body temperatures of 37-40 degrees Celsius and rapidly hardens and stay in place. In a sixth embodiment, such a reverse thermal mixture at 20 degrees C. is directly injected into hepatic metastases of primary tumors originating elsewhere, or into soft tissue metastases from breast or other primary cancers, and rapidly hardens to locally irradiate the injected tissue into which it is fixed. The precise combination will vary depending upon the tissues used, and would be determined empirically—the labelled hyaluranon supplying the therapeutic radiation.

In these embodiments, the conjugate (herein abbreviated "CogelRad-(Isotope)") could be tested in humans in a Phase 0 model, that is, using surrogate isotopes such as Technetium or Indium in clinically minute, definitively subtherapeutic amounts, during valid surgical or other procedures scheduled in these patients, and after obtaining informed consent as volunteers for additional maneuvers to determine proof of principle, and possibility of efficacy, of a new treatment so as to pave the way for a formal clinical trial.

In one embodiment of such a trial 200-300 ml solution of CoGelRad-Tcm99 is instilled into the bladder of a fluid-deprived subject just after voiding through a Foley Catheter, which is sealed off and allowed to remain for 30 minutes, after which it is flushed until less than 1% of injected radioactivity is judged to remain. If available, cystoscopic biopsies of normal and cancerous bladder tissue are obtained and sampled for radioactivity and histologic change. Samples of blood and urine are tested for leakage of radioactivity into the blood stream. This paves the way for a formal Phase I of Yttrium-90 in escalating doses up to 100 mCi per dose.

In another embodiment, patients with recently surgically debulked Ovarian Carcinoma will undergo placement of two intraperitoneal ports, for instillation of postoperative chemotherapy. At that time, usually at 2-3 weeks postoperatively, subtherapeutic doses of CoGelRad-Tcm99 is instilled into the abdomen in 1-2 liters of saline or similar isosmotic fluid, and monitored for uniformity of dispersal and leakage of radioactivity into the bloodstream. At 12 h post injection, the fluid is sampled to determine if a reasonable gradient of >20:1 exists between the peritoneal cavity and the blood, paving the way for a similar "second look" maneuver at six (6) months, this time with escalating doses of CogelRad-Y (up to 100 mCi in 0.1-0.5% Isotonic saline or Icodextrin solution) given with full shielding, and appropriate radiation precautions.

In yet another embodiment, patients with disseminated neoplasm confined to the abdominal cavity that have undergone debulking surgery and have had ports placed for intraperitoneal chemotherapy, undergo radiological study with thin barium three weeks postop to determine distribution of injected material, after which they are given subtherapeutic doses of CogelRad-Y given as additional therapy.

In still another embodiment, synovial spaces of patient with refractory synovial inflammatory proliferation are injected with subtherapeutic doses of CogelRad-Technetium, and if the distribution is adequate, and systemic and local leakage is minimal, three days later they receive a single injection n of 10-15 mCi of CogelRad-Y 0.1-1.0% solution, sufficient to sclerose the joint space.

In yet another embodiment, CogelRad-Y material is used specifically to augment radiation of the surgical fossa created around the superior mesenteric artery during Whipple Pancreatectomy procedure to effect additional local control, previously only achievable with great difficulty with brachytherapy (no longer used).

In one embodiment, the polymer is introduced into the bladder of a male through a Foley catheter as a non-thermal dependent liquid. It is held there by closing of the catheter. In one embodiment, the prepared abdominal cavity receives an injection of HA-DOTA-Yttrium in an appropriate concentration determined by the treating nuclear medicine specialist. In one embodiment, the concentration of HA-DOTA-Yttrium is low, less than 0.1%, depending upon the specific radioactivity of the conjugate. As HA is not radioactive, it is well tolerated in the operations above. In one embodiment, injections into the female bladder comprise or are applied with a temperature sensitive gel. A similar non-radioactive temperature-sensitive gel has undergone testing in man and is well tolerated but tumoricidally ineffective. The bladder of a subject can easily be irrigated with room temperature saline to wash out the now liquefied construct. In one embodiment, the subject is a human or an animal, such as a mouse.

In one embodiment, a temperature-sensitive gel is injected directly into a soft tissue adjacent to a tumor site, or directly into a metastasis in the liver or subcutaneous tissue. The injection would be through a polyethylene catheter at room temperature when the polymer complex (or construct) is a liquid, and where it would instantly gel upon injection into a nodule at a desired temperature. In one embodiment, the desired temperature is at least 7 degrees above its programmed gelation temperature of 37 degrees. In one embodiment, the desired temperature is 25 to 45° C. after gelation. In one embodiment, the gel is removed after a radiation for a pre-determined time. In one embodiment, the gel is removed at a time a target outcome is achieved or expected. In one embodiment, the pre-determined time ranges from half hour to 24 hours. In one embodiment, the pre-determined time ranges from a few hours(intraabdominal) to a few days (intraarticular). In one embodiment, the treatment is repeated at intervals ranging from one to three weeks up to as many as six doses.

Summarizing the foregoing, the present invention provides compositions and methods to employ a hyaluronan-based structure for modifying and administering radiotherapy to body cavities and associated structures. The method of its use, namely to inject or instill the HA-DOTA-radioactive construct alone or a temperature-sensitive hydrogel with HA as a carrier for a radioisotope provides superior treatment methods and advantages. The composition will remain largely confined to the cavity in which it is injected, including the bladder, peritoneal cavity, synovial cavity, and in gel form into secondary cavities, such as the lesser sac and origin of the superior mesenteric artery, or liver or soft tissues. This formulation may also include HA, carboxymethylcellulose (CMC), or other similar or related polymers of other molecular weights conjugated with DOTA, which can form increasingly viscous or gel like fluids or can be admixed with other materials such as GELFOAM® to conform appropriately to different spaces for appropriate radiotherapy.

An additional, incomplete listing of advantages of this compound over other formulations, for example, Avirad-Y® includes:

1. Hyaluranon is a better defined homogeneous polymeric molecule of known easily modifiable structure, molecular weight, and charge, and associated properties such as viscosity.
2. This construct can be easily doubly labelled with other determinants as well as DOTA, or short-half-life tracers such as Technetium, or MRI reagents such as Gallium.
3. An additional advantage of the proposed polymer is that it can accommodate more than one type of chemical group. In addition to the radioactive moiety, the molecule could also accommodate fluorophores such as fluorescein or rhodamine in order that the treating physician or surgeon can view immediate evidence of escape of conjugate from the bladder or synovial cavity. The radiotherapy moiety can be combined with other non-radioactive molecules such as Technetium-99 for preliminary phase 0 testing.
4. HA is routinely used as a vehicle in eye drops, and is used, in conjunction with carboxymethyl cellulose as well as an additive to many edible and cream products, and as such will more likely to be confined to the body cavity into which it is injected in a predictable manner, without undue retention (as with Avidin-Biotin) or loss due to antibody formation.
5. In contrast to other DOTA-conjugated antibodies or targeting molecules, CogelRad-Y can be injected and withdrawn from the body, thus greatly reducing systemic exposure.
6. The preparation of a Technetium analog is safe and straightforward, and yttrium 90, although a strong beta, is an agent for which plastic to glass sheeting will afford effective protection from the powerful short range beta radiation of yttrium 90.
7. Although the above discussions deal mainly with beta-emitting isotopes, the recent advances in preparation of DOTA conjugates with Actinium-225, an alpha-emitter, can be advantageously used for the treatment of cancer in intracavitary spaces and small metastatic nodules with ultra-short-range highly potent cytotoxic effectiveness against cancer.
8. Although very many potential uses for such an invention are possible, none has proposed its use as a device rather than a drug in which the hydrogel serves merely as a scaffold for the radiotherapeutic moiety. In particular, this combination has never been proposed for the treatment of bladder cancer or intraperitoneal cancer. Examples of these diseases have been given to illustrate the advantages of such a combination.

9. For bladder cancer, it is proposed that the drug be introduced into the bladder of a fluid deprived patient casted cavity via a Foley catheter, the dosage comprising up to about 100 mCi of yttrium-90 chelated in the DOTA moiety of the appropriate scaffolding molecule. This chemotherapeutic solution would be allowed to remain for up to six hours, after which it would be evacuated in its entirety (that is until less than 1% radioactivity remains in the wash) and the patient kept overnight and then sent home.

In one embodiment, the present invention provides a compound with the following structure:

T-DOTA-R, wherein T is a carbohydrate polymer bound to dodecane tetraacetic acid (DOTA) or a conjugate base thereof, and R is a radioactive isotope.

In one embodiment, the radioactive isotope is Yttrium-90, Technetium-99(m), Gadolinium-68, actinium-225, lutetium-177, indium-111, or ytterbium-169 and said carbohydrate polymer is a cellulose or derived cellulose.

In one embodiment, the carbohydrate polymer has a molecular weight ranging from 100,000 Da to 7,000,000 Da.

In one embodiment, the carbohydrate polymer is hyaluronic acid or a derivative thereof.

In one embodiment, the carbohydrate polymer is selected from hydroxypropyl methylcellulose (HPMC), hydroxypropyl cellulose (HPC), hydroxypropyl methylcellulose acetate succinate (HPMCAS), methyl cellulose, ethyl cellulose, carboxymethyl cellulose (CMC), cellulose acetate, cellulose acetate butyrate, hydroxyethyl cellulose (HEC), any salts thereof.

In one embodiment, the present invention provides a composition for treating a body cavity cancer, wherein said composition comprises the compound, wherein the compound is unable to penetrate membranes of the body cavity and is substantially confined within the body cavity.

In one embodiment, the compound after introduction into the body cavity achieves a concentration gradient between the peritoneal cavity and the blood of no less than 20:1.

In one embodiment, the composition comprises between 20% and 30% (w/w) ethylene oxide/propylene oxide block copolymer, between about 0.1% and about 0.3% (w/w) (HA-DOTA-R), between about 0.1% and about 1.8% (w/w) PEG-400, with the balance being water.

In one embodiment, the composition comprises between about 0.05% to about 0.8% hyaluronic acid (HA), between about 0.1% to about 2.5% PEG 400, and between about 18% to about 40% (w/w) ethylene oxide/propylene oxide block copolymer, with the balance being water.

In one embodiment, the composition comprises between about 12 and about 30% (w/w) Pluronic F127, between about 5 and about 30% (w/w) Pluronic F68, between about 0.05% and about 2% (w/w) CMC, and between about 0.1% and about 2.5% (w/w) PEG-400, with the balance being water.

In one embodiment, the present invention provides a method for treating body cavity cancer in a patient, comprising:
a) introducing through a Foley catheter into the body cavity of the patient an effective amount of a composition comprising the following structure:

T-DOTA-R, wherein T is a carbohydrate polymer bound to dodecane tetraacetic acid or a conjugate base thereof, and R is a radioactive isotope, wherein the compound is confined within the body cavity and unable to pass through membranes in the body cavity.

In one embodiment, the radioactive isotope is Yttrium-90, Technetium-99(m), Gadolinium-68, actinium-225, lutetium-177, indium-111, or ytterbium-169, and said carbohydrate polymer is a cellulose or derived cellulose.

In one embodiment, the carbohydrate polymer is selected from hyaluronic acid (HA), hydroxypropyl methylcellulose (HPMC), hydroxypropyl cellulose (HPC), hydroxypropyl methylcellulose acetate succinate (HPMCAS), methyl cellulose, ethyl cellulose, carboxy methylcellulose (CMC), cellulose acetate, cellulose acetate butyrate, hydroxyethyl celluloses (HEC), any salts thereof.

In one embodiment, the body cavity cancer is bladder cancer, peritoneal cancer, appendiceal carcinoma, or ovarian carcinoma.

In one embodiment, the compound after introduction into the body cavity achieves a concentration gradient between the peritoneal cavity and the blood of no less than 20:1.

In one embodiment, the radioactive isotope emits to an affected region of said body cavity a radiation of about 30 CgY.

In one embodiment, the present invention provides a method for treating body cavity cancer in a patient, comprising:
a) introducing into the body cavity of the patient an effective amount of a composition forming a hydrogel on the inner wall of the body cavity, wherein said composition comprises a compound with the following structure:

T-DOTA-R, b) allowing said hydrogel to emit a radiation to an affected region of said body cavity for a predetermined time; and
c) sufficiently removing the hydrogel from the body cavity;
wherein T is a carbohydrate polymer bound to dodecane tetraacetic acid or a conjugate base thereof, and R is a radioactive isotope, wherein the compound is confined within the body cavity and unable to pass through membranes in the body cavity.

In one embodiment, the hydrogel is formed in situ after the composition in liquid is introduced into said body cavity.

In one embodiment, the hydrogel comprises hyaluronic acid (HA), either alone or covalently bound to said compound.

In one embodiment, the predetermined time is about 0.5-20 hours.

In one embodiment, the hydrogel is removed from the body cavity by a cold rinse of 20° C., which is used to liquefy the hydrogel.

In one embodiment, the invention provides a compound with the following structure:

T-Linker-Chelator-R, wherein T is a carbohydrate polymer, Linker is for example ADH, Chelator is DOTA, DTPA, etc., and R is radioactive isotope.

Although the invention has been described in conjunction with specific embodiments thereof, it should be apparent to one of skill in the art that many alternatives, modifications, and variations will be apparent upon review of this disclosure. It is therefore intended to embrace all such alternatives, modifications, and variations that fall within the spirit and scope of the invention as defined by the following claims.

I claim:

1. A composition for treating a body cavity cancer, comprising a compound having the following structure:

T-DOTA-R, wherein T is cellulose or hyaluronic acid or derivatives thereof, bound to dodecane tetraacetic acid (DOTA) or a conjugate base thereof, and R is Yttrium-90, Lutetium-177, Technicium-99(m), or Actinium-225, and wherein the composition is unable to penetrate through outer membranes of the body cavity and is substantially confined within the body cavity, wherein said composition comprises between 20% and 30% (w/w) ethylene oxide/propylene oxide block copolymer, between about 0.1% and about 0.3% (w/w) (HA-DOTA-R), between about 0.1% and about 1.8% (w/w) PEG-400, with the balance being water.

2. The composition of claim 1, wherein the radioactive isotope is Yttrium-90 or Technetium-99(m), and T is cellulose or derived cellulose.

3. The composition of claim 1, wherein T has a molecular weight ranging from 100,000 Da to 7,000,000 Da.

4. The composition of claim 1, wherein T is hyaluronic acid or a derivative thereof and R is Yttrium-90, Lutetium-177 or Actinium-225.

5. The composition of claim 1, wherein T is hyaluronic acid (HA), hydroxypropyl methylcellulose (HPMC), hydroxypropyl cellulose (HPC), hydroxypropyl methylcellulose acetate succinate (HPMCAS), methyl cellulose, ethyl cellulose, carboxymethyl cellulose (CMC), cellulose acetate, cellulose acetate butyrate, hydroxyethyl cellulose (HEC), or any salts thereof.

6. The composition of claim 1, wherein the compound after introduction into the peritoneal cavity achieves a concentration gradient between the peritoneal cavity and the blood of no less than 20:1.

7. A composition for treating a body cavity cancer, comprising a compound having the following structure:

T-DOTA-R, wherein T is cellulose or hyaluronic acid or derivatives thereof, bound to dodecane tetraacetic acid (DOTA) or a conjugate base thereof, and R is Yttrium-90, Lutetium-177, Technicium-99(m), or Actinium-225, and wherein the composition is unable to penetrate through outer membranes of the body cavity and is substantially confined within the body cavity, wherein said composition comprises between about 0.05% to about 0.8% hyaluronic acid (HA), between about 0.1% to about 2.5% PEG 400, and between about 18% to about 40% (w/w) ethylene oxide/propylene oxide block copolymer, with the balance being water.

8. The composition of claim 7, wherein the radioactive isotope is Yttrium-90 or Technetium-99(m), and T is cellulose or derived cellulose.

9. The composition of claim 3, wherein T has a molecular weight ranging from 100,000 Da to 7,000,000 Da.

10. The composition of claim 7, wherein T is hyaluronic acid or a derivative thereof and R is Yttrium-90, Lutetium-177 or Actinium-225.

11. The composition of claim 7, wherein T is hyaluronic acid (HA), hydroxypropyl methylcellulose (HPMC), hydroxypropyl cellulose (HPC), hydroxypropyl methylcellulose acetate succinate (HPMCAS), methyl cellulose, ethyl cellulose, carboxymethyl cellulose (CMC), cellulose acetate, cellulose acetate butyrate, hydroxyethyl cellulose (HEC), or any salts thereof.

* * * * *